United States Patent [19]

Becker et al.

[11] 4,049,503

[45] Sept. 20, 1977

[54] ELECTROCHEMICAL GAS DETECTION

[75] Inventors: Wolf-Jürgen Becker; Wolfram Breuer, both of Leverkusen; Jacques Deprez, Frechen, all of Germany

[73] Assignee: Bayer Aktiengesellschaft, Leverkusen, Germany

[21] Appl. No.: 598,601

[22] Filed: July 24, 1975

[30] Foreign Application Priority Data

July 27, 1974  Germany .................... 2436261

[51] Int. Cl.² .......................... G01N 27/46
[52] U.S. Cl. .................... 204/1 T; 204/195 R; 204/195 S
[58] Field of Search ........... 204/1 T, 1 Y, 1 P, 1 S, 204/1 B, 1 N, 1 K, 1 F, 1 W, 1 E, 195 R, 195 P, 195 S, 195 M, 195 B; 136/157, 158

[56] References Cited

U.S. PATENT DOCUMENTS

| | | | |
|---|---|---|---|
| 3,160,577 | 12/1964 | Nolan | 204/195 |
| 3,258,415 | 6/1966 | Kordesch | 204/195 |
| 3,272,725 | 9/1966 | Garst | 204/1 P |
| 3,785,948 | 1/1974 | Hitchman et al. | 204/195 P |
| 3,857,760 | 12/1974 | Breuer et al. | 204/1 T |
| 3,912,614 | 10/1975 | Spracklen et al. | 204/195 B |

Primary Examiner—G. L. Kaplan
Attorney, Agent, or Firm—Burgess, Dinklage & Sprung

[57] ABSTRACT

In the gas detector the gas stream to be investigated is conveyed past one of two electrodes of a measuring cell. The two electrodes are in contact with an electrolyte, wherein the electrolyte is an anhydrous organic gel. The gas component to be measured changes the electrochemical equilibrium at one of the two electrodes and produces thereby in the outer closing circuit a measurable electrical current which is a measure of the concentration of the gas component, to be detected.

54 Claims, 3 Drawing Figures

ELECTROCHEMICAL GAS DETECTION

This invention relates to an electrochemical gas detector for measuring traces of a gas in a gas mixture.

The control of environmental pollution (i.e. time changes and local changes in the natural state of the environment, brought about for example by processes for synthesizing various products in the chemical industry) can only be carried out if the physical and material changes in the air can be quantitatively detected, if possible continuously. In order to achieve this, numerous compounds have to be unequivocally detected. Many of these impurities have to be detected in extremely dilute form (from one part per million to one part per thousand million). The present invention is concerned with detecting and measuring gas traces as small as these.

Electrochemical methods are frequently used for analysing traces of gases. In methods of this kind, the measuring electrode of a galvanic cell is brought into contact with the gas to be examined, producing an electrical current which is proportional to the compound to be measured. In cases where a reducible gas (for example oxygen, nitrogen dioxide, ozone or chlorine) is measured, there is a reaction on a measuring electrode acting as cathode, whilst oxidisable gases (for example hydrogen sulphide, hydrogen cyanide or sulphur dioxide) are reacted on a measuring electrode acting as anode.

In cases where measurment is carried out at normal room temperature, it has hitherto been common practice to use aqueous electrolyte systems. One disadvantage of using aqueous electrolyte systems for the automatic analysis of gases is their considerable vapour pressure. In aqueous electrolytes of this kind, there is an exchange between water vapour and the test gas stream which can lead either to a loss of water or to the uptake of water by the electrolyte and, hence, to the concentration or dilution of the electrolyte and to a considerable loss of mass.

The advantages of using solid, organic electrolytes for measuring gases are described in detail in German Pat. No. 1,773,795. This electrolyte is a solid substance consisting of a crystalline structure and an "active" liquid phase present therein in which dissociation, ion transport and chemical reactions take place.

The crystalline structure of the electrolyte represents an additional electrical equivalent resistance for the measuring system.

Another disadvantage of this electrolyte is its often inadequate diaphragm effect. A gas can penetrate through the crystalline structure to the counterelectrode without reacting on the measuring electrode, thereby weakening the measuring effect.

The object of the invention is to provide a water-free organic solid electrolyte with improved electrochemical and mechanical properties.

According to the invention, there is provided an electrochemical gas detector for measuring traces of gases in a gas mixture, in which the gas stream to be examined is guided past one of two electrodes of a measuring cell which are both in contact with an organic electrolyte and the gas component to be measured changes the electrochemical equilibrium at one electrode, thereby generating a measurable electrical current between the two electrodes in an outer closing circuit, wherein the electrolyte is an anhydrous organic gel. An organic gel may be obtained by the action of an anhydrous organic solvent on a synthetic polymer. It is preferred to use linear-macromolecular polymers whose chain length corresponds to a molecular weight of at least 50,000. The gel advantageously has an electrical conductivity of at least $10^{-5}$ ohm$^{-1}$ cm$^{-1}$, a dielectric constant of more than 20 and a dipole moment of more than 2.0 Debye.

According to another embodiment of the invention, the gel is doped with a salt, which dissociates in the organic solvent for the polymer in order to adjust its electrical conductivity.

In many cases, it is also of advantage to provide the gel with other additives in order to catalyse the reactions at the electrodes and to make available ions with which the gas component to be measured can react, and also in order to adjust an electrode potential so that a reaction can take place with the gas component to be measured, and in order to exert an inhibiting effect upon the reaction with other gas components Preferred solvents for the polymer are organic compounds containing a carbonyl, alkoxyl, hydroxyl or phosphonic acid ester group. Suitable polymers are homopolymers are copolymers of olefinically unsaturated compounds, more especially monovinyl or monovinylidene monomers.

Special embodiments of the invention for detecting specific gas components are described in the Subsidiary Claims.

ORGANIC GELS

The gel phase is defined as a particular aggregate state of colloidal systems characterised, in contrast to liquid "sols", by the coherence of the dispersed substance (J. Stauff, Kolloidchemie, Spring er-Verlag, Berlin - Gottingen - Heidelberg (1960), page 665).

A gel is a solid or semi-solid colloid containing a considerable quantity of liquid. The colloid consists of particle containing from $10^3$ to $10^9$ atoms. The particles in a gel are linked together to form a coherent network which makes the liquid immovable (B. Jirgenson, Organic Colloids, Elsevier Publishing Comp., Amsterdam - London - New York - Princeton (1958), page 8.).

Gels are defined as colloidal systems of at least two components in which 1. the dispersed substance (or the colloid (Stauffs op. cit., p. 439)) and the dispersant (solvent) both form cohesive (coherent), interpenetrating systems,
2. the system as a whole does not have the character of a liquid,
3. the conditions of a disperse system apply (Stauff, op. cit., pg. 666) (in a disperse system, the final particle volume of the dispersed substance is greater than the particle volume of the dispersant molecules (Stauff, op. cit., p. 439)), and
4. a final mixing entropy prevails, these coherent colloidal systems cannot be swollen and deswollen (Stauff, op. cit., p. 439). The dispersed substance or the colloid may be solvated (Stauff, op. cit., p 682). Each dissolved molecule tends to become surrounded by a shell of solvent molecules. In this case, experts often speak of solvation (H. A. Stuart, Die Physik der Hochpolymere, Vol. 2 Das Makromolekul in Losungen, Springer-Verlag, Berlin - Gottingen - Heidelberg (1953), page 102) or solvent coating (B. Jirgenson, op, cit., pp. 58-59; J. Eggert, Lehrbuch der Physikalischen Chemie, S. Hirzel Verlag, Struttgart (1960), p. 405).

When a solid linear macromolecular substance is treated with a solvent, the filamentary molecules are not immediately dissolved out, instead the solvent molecules penetrate between the filamentary molecules and solvate them before they have acquired their free mobility. Accordingly, a swollen gel is initially formed from a substance of this kind when solvents are added to it (H. A. Stuart, op. cit., p. 262).

A gel is a state between a solid and a solution which is only possible with linear colloids. In such a state, the solvent molecules are uniformly distributed between the macromolecules. In other words, the macromolecules are dissolved like the molecules in a concentrated solution of a low molecular weight substance. However, to be "properly" dissoved, the filamentary molecules must have space available which corresponds to their wide range of activity (volume occupied by one filamentary molecule in solution). This is not possible in the gel state. Thus, the gel state is similar to the solid state in regard to the mobility of the filamentary molecules, because the filamentary molecules are unable to oscillate in all directions, but instead are only really rotatable about their longitudinal axes. As already mentioned, an organic polymer will only form a gel under certain conditions according to Staudinger, namely:

a. the colloid particles are macromolecules (molecular colloid); accordingly, molecular colloids are solutions of macromolecular substances;
b. the molecules have an elongated particle configuration (linear colloids);
c. the remarkable property of swelling, i.e. gel formation, is only shown by the group of linear-macromolecular substances with long filamentary molecules (number of chain members $\geq$ 2000 corresponding to a molecular weight of $\geq$ 50,000) (H. Staudinger, Die Wissenschaft, Vol. 93: Organische Kolloidchemie, Friedr. Vieweg & Sohn, Braunschweig (1950), p. 286).

Since only organic solvents are used, the choice of polymers is confined to homopolar compounds (H. Staudinger, op. cit., p. 286).

DOPING AND ELECTROLYTE ADDITIVES

The electrolyte must be sufficiently electrically conductive ($> 10^{-5}$ ohm$^{-1}$cm$^{-1}$) to allow the transport of electrical current between the electrodes. The solvent must have both an ioninzing and a dissociating effect upon any doping agent AB added. This can be achieved either through a sufficiently high dielectric constant or polarity and molecular structure of the solvent. The dissolution of a salt AB in a solvent S is accompanied by ionization of the molecule AB and by the formation of solvated pairs of ions $$nS + AB \rightleftarrows nS, A^-B^+$$

and by dissociation of one pair of ions into free ions $$nS, A^-B^+ \rightleftarrows n'S, A^- + n''S, B^+$$

where $n' + n'' = n$.

Each stage is described by an equation. Solvation is expressed by the equation:

$$K_s = \frac{[AB]}{[A^-B^+]},$$

whilst the dissociation of a pair of ions takes place in accordance with the following equation:

$$K_D = \frac{[A^-][B^+]}{[A^-B^+]}$$

where [A$^-$B$^+$], [A$^-$], [B$^+$] indicates the concentration of the various solvated types.

With the aid of the dielectric constant $\epsilon$, the dissociation constant $K_D$ is expressed by the following equation:

$$pK_D = pK_o + 0.45 \frac{Ne^2}{RT} \frac{Z_1 \cdot Z_2}{r_1 + r_2} \frac{1}{\epsilon},$$

where
$pK_D = -\log_{10} K_D$,
$pK_o = $ const.,
$Z_1, Z_2$ ion charge,
$r_1 + r_2$ minimal interval between the two ions,
$e = $ elementary charge,
$N = $ Loschmidt's constant
$R = $ universal gas constant and
$T = $ absolute temperature It can be seen from the equation that, for a given concentration of a certain salt, the concentration of ions in the electrolyte increases with the dielectric constant. On the other hand, the following equation exits between the free ions A$^-$ and B$^+$, the non-dissociated salt AB and the pair of ions A$^-$ B$^+$:

$$K_c = \frac{[A^-][B^+]}{[AB] + [A^-B^+]} = \frac{K_D}{1 + K_s}$$

In cases where a salt of low dielectric constant is used, it is necessary, as apparent from the last equation, to use a solvent of low $K_s$ in order to keep the value of $K_c$ constant. For a given solvent, the value of $K_s$ is governed by its polarity and molecular structure. If polarity and molecular structure are such that an ion is readily solvated, the solvent will heavily ionize the salt. Salts with minimal binding energy are of interest in this respect. Since this energy changes with the reciprocal sum of anion and cation radius, this sum must be maximal. Accordingly, potassium hexafluorphosphate (KPF$_6$) was used as test substance for doping solvents.

In addition, salts acids and bases are used as electrolyte additives in order to influence the electrochemical mechanism at the electrodes. The electrolyte additives perform the following functions:

1. the reaction of the electrodes is catalysed,
2. ions with which the gas component to be measured can react are made available in the electrolyte,
3. the electro-potential at which a reaction can take place with the gas component to be measured is adjusted, and
4. an inhibiting effect is exerted upon the reaction with other gas components.

In the solid electrolyte described in W. Breuer, J. Deprez, B. Sturm, Analysengerat zur Messung von Gaskonzentrationen, DT-PS No. 1,773,795, Application filed: 8.7.68, Laid open: 10.5.72, the components of the electrolyte produce solidity by crystal formation. The choice of electrolyte mixtures is restricted. One or more components of the electrolyte was intended to produce a fine, dense crystalline network in which the liquid electrolyte is trapped. There is no longer any need for this with the new gel electrolytes of the present invention.

The gel electrolyte affords the following advantages over the solid electrolyte referred to above:

a. Electrochemical Properties

1. The proportion of liquid phase in the total electrolyte mass is considerably greater (conventional electrolyte 30-50%, gel electrolyte more than 85% by weight). This affords the following advantages:
   the conductivity of the electrolyte is considerably greater;
   the mass lost through evaporation is reduced in relative terms.
2. Since there is no longer any need for a crystalline network to be formed, the choice of electrolyte mixtures is considerably widened.
   the detector was improved in regard to selectivity, speed of indication and zero-point behaviour;
   new components can be detected and measured;
   it is possible to apply other measuring principles in addition to the galvanic-cell measuring principle (concentration element or redox system), for example depolarization current measurment (Example 6);
   the measuring range is widened by virtue of the greater load capacity for the gases to be measured.
3. In the conventional solid electrolyte, the gas is able to penetrate through the crystalline structure without dissolving. The gel does not have any pores, so that gas can only be transported in dissolved form. Accordingly, it is now no longer possible for the gas to diffuse through the gel to the counterelectrode, in other words the diaphragm effect of the electrolyte has been improved.

b. Mechanical Properties

The plasticityand pourability of the electrolyte when it is hot enable it to be made up into any shape. As a result, the electrolyte can be prepared for subsequent incorporation in a cell. Renewal of the measuring cell is confined to changing the electrolyte. Accordingly, production and maintenance are simple and inexpensive to carry out.

Since the gel electrolyte is an intermediate stage between a solid and a liquid phase, optimum embedding of the electrode is possible. The triple phase interface (gas, electrode, electrolyte) can be considerably enlarged.

A gel makes it possible to use new kinds of electrode such as the application of conductive powders to the electrolyte. These electrodes have a high level of activity (high area).

Depending upon the gas component to be detected and the external conditions, it can be of advantage to use different electrode forms, for example vapour-coated or sintered electrodes, membranes, woven fabrics and sieves. Electrodes of this kind enable the measuring cells to be miniaturized.

CHEMICAL COMPOSITION OF A FEW SPECIAL GEL ELECTROLYTES

Experimmental testing of the anhydrous organic gel as electrolyte was carried out on the basis of the following three parameters:

1. gel formation of polymers by adding different solvents (Table 1).
2. ionic conductivity of solvents by the addition of a conducting salt, for example potassium hexafluorophosphate $KPF_6$ (Table 2).
3. changes in the ionic conductivity of gels by adding $KPF_6$ (Table 3).

In addition, exemplary embodiments of gel electrolytes for different gas components were tested in combination with different electrode materials; the selectivity of the gas detector for the gas component to be measured was improved by controlled doping of the gel electrolyte (cf. Examples 1 and 2).

Exemplary embodiments of the invention are described in more detail in the following with reference to the accompanying drawings, in which.

The gel electrolyte measuring cells are intended to be simple in structure, easy to maintain and inexpensive. These objectives can be achieved by standardising various components, by simplifying design and by ensuring that the components may readily be replaced. In particular, the electrolyte and electrodes are intended to be readily replaceable.

Two different designs have been developed for the detector according to the function which it is intended to perform. Through flow measuring cells are used for measurements requiring a high degree of accuracy. In this embodiment, gas is transported by admitting the gas to be measured under suction. In monitoring systems (for example for monitoring ambient air), it is possible to use diffusion measuring cells (remote measuring head) which are much simpler in design. In this case, the gas is transported by diffusion. Since no separate gas transport system is required, this embodiment is simpler.

Figure 1:
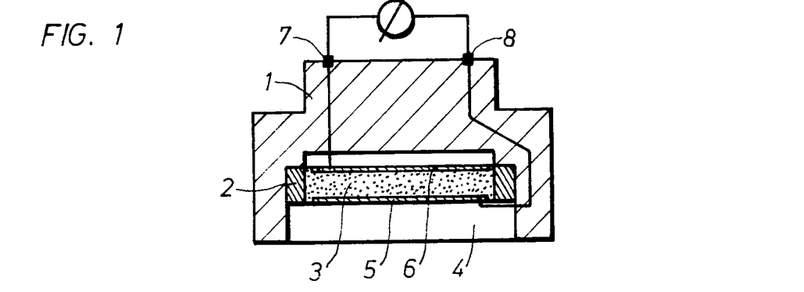
FIG. 1 shows the layout of a measuring cell.

As shown in FIG. 1, the diffusion measuring cell consists of a polyethylene cylinder 1 accommodating the electrochemical measuring system. A polyethylene ring 2 surrounds the gel electrolyte 3. A measuring electrode 5 is embedded in the electrolyte on the outside 4 of the hollow space in the cylinder, whilst a counter-electrode 6 is embedded on the inside. The electrodes are connected to electrical terminals 7 and 8. After the gas has passed through the hollow space 4, it reacts at the interface between the electrolyte 3 and the electrode 5. The change in the electrochemical equilibrium between the two electrodes produces a measurable electrical current in the outer closing circuit between the electrical terminals 7 and 8, which is a measure of the concentration of the gas component to be detected If it is intended to use the measuring cell as a throughflow measuring cell, the arrangement described above is fitted into the attachment shown in FIG. 2. The gas stream to be investigated is passed through a bore 10 and a gas duct 11 in a plastics throughflow element 9 and leaves the hollow space 12 through the bore 13.

Figure 2:
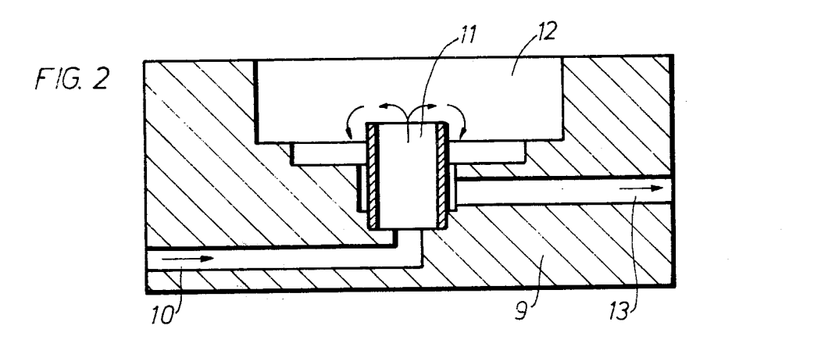
FIG. 2 shows an arrangement in which the measuring cell is in the form of a throughflow cell.

By comparison with conventional measuring cells, it is possible with these embodiments to obtain all the advantages referred to on the preceding pages, such as simplification of the measuring system, reusability of the mechanical components, standarization of the throughflow and diffusion measuring cells. In the event of failure of the measuring cell, repair work is confined to replacing the gel electrolyte 3.

EXAMPLE 1 ($H_2S$, $COCl_2$, HCN)

Throughflow and diffusion measuring cells were designed for determining hydrogen sulphide, phosgene and hydrocyanic acid in the so-called trace range (1 ppb to 10 ppm). The above components could be individually detected by means of suitable chemical selective filters.

The gel electrolyte consists of the polymer polymethyl methacrylate (10.0% by weight), the solvent propylene carbonate (87.0% by weight), the electrolyte — consisting of benzoic acid (2.0% by weight) and sodium benzoate (0.5% by weight) — and the doping agent iron (III) sulphate (0.5% by weight). This mixture is dissolved at 100° C and poured into a mould. The mass gels on cooling.

Doping of the gel electrolyte with iron (III) sulphate $Fe_2(SO_4)_3$ increases it selectivity. Doping in this way enabled the influence of atmospheric moisture on zero-point behaviour to be considerably reduced. With a non-doped gel electrolyte, doubling relative humidity from 20% to 40% produced a change in the zero-point current from 6 nA to 8.8 nA, whereas in the case of doped gel electrolytes, the zero-point current was changed from 0.1 to 0.8 nA.

The gel electrolyte is arranged between two silver cloths which act as electrodes, and can be used in a diffusion measuring cell according to FIG. 1 or in a throughflow measuring cell according to FIG. 2.

EXAMPLE 2 ($SO_2$)

Sulphur dioxide was measured in the same way as in Example 1. The gel electrolyte consists of polyacrylonitrile (16.4% by weight), γ-butyrolactone (73.0% by weight), triethanolamine (9.0% by weight), acetic acid (1.2% by weight) whilst the doping agent consists of silver sulphate $Ag_2SO_4$ (0.4% by weight). The sensitivity of the gel electrolyte was increased by a factor of 10 to 20 by doping in this way.

EXAMPLE 3 ($NO_2$)

The measurement of nitrous gases (for example $NO_2$) is carried out with the same layout of the measuring cell as in Example 1. The gel electrolyte consists of polymethyl methacrylate (10% by weight), phosphoric acid trisdimethyl amine (85% by weight) and potassium hexaflurophosphate (5% by weight). The measuring electrode is a gold sieve, the comparison electrode a carbon plate.

EXAMPLE 4 ($O_2$)

Traces of oxygen may be measured with a layout of the measuring cell similar to that used in the preceding Examples. The gel electrolyte consists of a mixture of polyacrylonitrile (12% by weight), propylene carbonate (80% by weight), triethanolamine (5% by weight) and acetic acid (3% by weight). A silver sieve is used as the measuring electrode and a lead plate as the comparison electrode.

EXAMPLE 5 ($H_2F_2$)

Hydrogen fluoride may be measured with the same layout of the measuring cell as described in Example 1. The gel electrolyte consists of polymethyl methacrylate (10% by weight), propylene carbonate (89% by weight) and acetic acid (1% by weight). The measuring electrode is coiled zirconium wire, and the counterelectrode a platinum plate.

EXAMPLE 6 ($Cl_2$)

Figure 3:
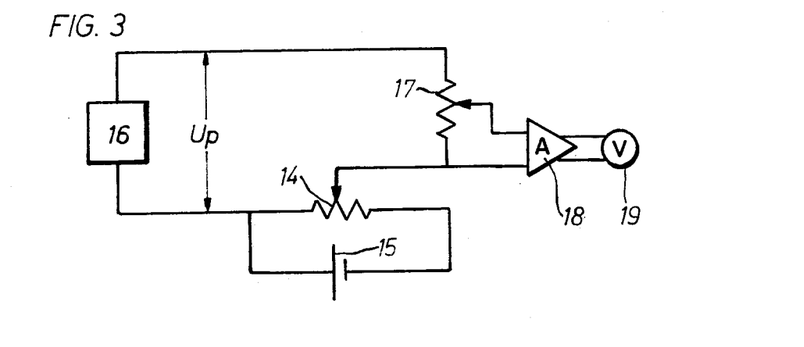
FIG. 3 shows an electrical measuring arrangement for measuring traces of chlorine gas.

Chlorine is measured by the method of depolarisation current measurement (cf. FIG. 3). A low voltage is applied to the electrodes of the Pt-electrode / gel electrolyte / Pt-electrode system, thereby building up a polarization layer at the measuring electrode (anode) so that no electrical current can flow. Any chlorine present in the gas to be analyzed oxidizes this layer, so that a depolarization current flows between the two polarized electrodes in the measuring cell. The intensity of this current is proportional to the concentration of the chlorine in the gas being measured and may be indicated. The layout of the measuring cell corresponds to that of Examle 1. The electrical measuring arrangement is illustrated in FIG. 3. A suitable polarization voltage $U_p$ is applied to a measuring cell 16 by means of a potentiometer 14 and a d.c. voltage source 15. A potentiometer 17 is used as working resitance for measuring the depolarization current. The potentiometer 17 is also used for adjusting the required sensitivity. The measuring signal may either be directly indicated by means of a voltmeter, although it is preferably amplified by means of a measuring amplifier 18 and indicated by an indicating instrument 19. The gel electrolyte consists of a mixture of polyacrylonitrile (18.0% by weight), propylene carbonate (81.3% by weight), potassium hexafluorphosphate (0.45% by weight), iron (III) sulphate (0.11% by weight) and lead (II) or cobalt (II) nitrate (0.14% by weight). The most favourable working point is at a polarization voltage $U_p$ of 100 mV where the zero current is only 1/300 of the measuring current produced by a $Cl_2$-concentration of 1 ppm.

TABLE 1

Gel formation of a few linear macromolecular vinyl derivatives with different solvents

| Solvent | Polymer PVC | PAN | PMMA | Remarks |
| --- | --- | --- | --- | --- |
| Acetoxy cyclohexane | + | − | + | |
| Ethylene glycol diacetate | + | − | − | |
| Benzoic acid ethyl ester | + | − | + | |
| γ-butyrolactone | + | + | + | |
| Caprolactone | − | + | + | |
| Diethylene glycol monobutyl ether | + | − | + | |
| 2,2-dimethyl-3-butanone | − | − | + | |
| 4,4-dimethyl-1,3-dioxane | + | − | + | |
| 2,2-dimethyl-4-hydroxy methyl-1,3-dioxolane | − | − | + | |
| 1-methyl-4-cyclohexanol | − | − | + | |
| Methyl cyclohexanone | − | − | + | isomer mixture |
| Methyl cyclohexyl acetate | + | − | + | isomer mixture |
| 1-methyl-2-pyrrolidone | − | + | + | |
| Lactic acid ethyl ester | + | − | + | |
| Oxalic acid diethyle ester | + | − | − | |
| Phosphoric acid-tris-dimethyl amide | − | + | + | |
| Propylene carbonate | + | + | + | |
| Butylene carbonate | + | + | + | |

+ = useable gel formed
− = no useable gel formed
PVC = polyvinyl chloride
PAN = polyacrylonitrile
PMMA = polymethyl methacrylate

TABLE 2

Volume resistivity of different solvents with and without 2% of $KPF_6$ added

| | Volume resistivity in Ω · cm | Doping Agent | |
| --- | --- | --- | --- |
| Solvent | None | 2% of $KPF_6$ | Remark |
| Benzoic acid ethyl ester | $>10 \times 10^6$ | $2 \times 10^6$ | |
| γ-butyrolactone | 700 | 420 | only partly soluble |
| Caprolactone | $350 \times 10^3$ | $1 \times 10^3$ | |

-continued

| Solvent | Volume resistivity in Ω·cm None | Doping Agent 2% of KPF$_6$ | Remark |
|---|---|---|---|
| Diethylene glycol monobutyl ether | 5×10$^6$ | 4×10$^6$ | |
| 4,4-dimethyl-1,3-dioxane | 1.5×10$^6$ | 10×10$^3$ | only partly soluble |
| 2,2-dimethyl-4-hydroxy methyl-1,3-dioxolane 5×10$^6$ | 1×10$^6$ | | |
| Methyl cyclohexanone | >10×10$^6$ | 1.5×10$^3$ | only partly soluble isome mixture |
| 1-methyl-2-pyrrolidone | 520×10$^3$ | 380 | only partly soluble |
| Lactic acid ethyl ester | 1.7×10$^6$ | 1.3×10$^3$ | only partly soluble |
| Phosphoric acid-tris-dimethyl amide | 100×10$^3$ | 800 | |
| Propylene carbonate | 170×10$^3$ | 250 | |
| Butylene carbonate | 250×10$^3$ | 520 | |

TABLE 3

Change in the volume resistivity of different electrolytes during gel formation

| Solvent | Volume resistivity in Ω·cm Electrolyte of solvent + 2% of KPF$_6$ | Gel Electrolyte of solvent + 2% by weight of KPF$_6$ and polymer | | | |
|---|---|---|---|---|---|
| | | % by weight | PAN(1) | % by weight | PMMA(2) |
| γ-butyrolactone | 420 | 10 | 600 | 16 | 400 |
| Caprolactone | 1.2×10$^3$ | 14 | 2×10$^3$ | 10 | 1.2×10$^3$ |
| Diethylene glycol monobutyl ether | 4×10$^3$ | — | —(3) | 10 | 4.6×10$^3$ |
| 1-methyl-2-pyrrolidone | 380 | 20 | 1000 | 10 | 390 |
| Lactic acid ethyl ester | 1.3×10$^3$ | — | —(3) | 10 | 1.5×10$^3$ |
| Phosphoric acid-tris-dimethyl amide | 800 | 20 | 3400 | 10 | 940 |
| Propylene carbonate | 380 | 20 | 1000 | 10 | 450 |
| Butylene carbonate | 520 | 20 | 1×10$^3$ | 10 | 500 |

Remarks
(1)PAN = polyacrylonitrile
(2)PMMA = polymethyl methacrylate
(3)no gel formation

What we claim is:

1. In an electrochemical gas detector for measuring traces of a component of a gas mixture comprising a cell comprising two electrodes and an organic electrolyte between and in contact with said electrodes, an outer closing circuit connected to said electrodes for flow of an electric current through the electrolyte and the outer closing circuit, said outer closing circuit including measuring means responsive to flow of current in the outer closing circuit, means for introducing a gas mixture into said cell, said cell being adapted for contacting the gas mixture with the electrolyte for changing the electrochemical equilibrium at one of the electrodes for generation of an electrical current in the outer closing circuit, the improvement which comprises said electrolyte consisting essentially of an anhydrous organic gel.

2. Detector of claim 1, wherein said anhydrous organic gel is based on an anhydrous organic solvent and a synthetic polymer.

3. Detector of claim 2, wherein the polymer is a linear-macromolecular substance whose chain length corresponds to a molecular weight of at least 50,000.

4. Detector of claim 2, wherein the polymer and solvent are homopolar molecules.

5. Detector of claim 2, wherein the gel is doped with a salt which dissociates in the organic solvent for the polymer.

6. Detector of claim 5, wherein the salt is KPF$_6$.

7. Detector of claim 2, wherein the organic solvent contains a carbonyl, alkoxyl, hydroxyl or phosphoric acid ester group.

8. Detector of claim 2, wherein the polymer is a homopolymer of an olefinically unsaturated compound, or a copolymer of olefinically unsaturated compounds.

9. Detector of claim 8, wherein the polymer is of at least one monomer of the group monovinyl monomers and monovinylidene monomers.

10. Detector of claim 2, wherein the polymer is polyvinyl chloride and the solvent is of the group acetoxy cyclohexane, ethylene glycol diacetate, benzoic acid ethyl ester, γ-butyrolwactone, diethylene glycol monobutyl ether, 4,4-dimethyl-1,3-dioxane, methyl cyclohexyl acetate, lactic acid ethyl ester, oxalic acid diethyl ester, propylene carbonate and butylene carbonate.

11. Detector of claim 2, wherein the polymer is polyacrylonitrile and the solvent is of the group γ-butyrolactone, caprolactone, 1-methyl-2-pyrrolidone, phosphoric acid-tris-dimethyl amide, propylene carbonate and butylene carbonate.

12. Detector of claim 2, wherein the polymer is polymethyl methacrylate and the solvent is of the group acetoxy cyclohexane, benzoic acid ethyl ester, γ-butyrolactone, caprolactone, diethylene glycol monobutyl ether, 2,2-dimethyl-3-butanione, 4,4-dimethyl-1,3-dioxane, 2,2-dimethyl-4-hydroxy methyl-1,3,-dioxolane, 1-methyl-4-cyclohexanol, methyl cyclohexanone, methyl cyclohexyl acetate, 1-methyl-2-pyrrolidone, lactic acid ethyl ester, phosphoric acid-tris-dimethyl adide, propylene carbonate and butylene carbonate.

13. Detector of claim 2, suitable for detecting hydrogen sulfide, wherein said one electrode comprises silver, and said polymer is polymethyl methacrylate or polyacrylonitrile, and said solvent is propylene carbonate, and the electrolyte contains as additive sodium benzoate and benzoid acid, and is doped with iron (III) sulphate.

14. Detector of claim 2, suitable for detecting hydrogen sulfide, wherein said one electrode comprises silver, and said polymer is polyacrylonitrile, and said solvent is γ-butyrolactone, and the electrolyte contains as additives sodium benzoate and benzoic acid and is doped with iron (III) sulphate.

15. Detector of claim 2, suitable for detecting hydrogen sulfide, wherein said one electrode comprises silver, said polymer is polymethyl methacrylate, and said solvent is propylene carbonate or phosphoric acid-tris-dimethyl amine, and the electrolyte contains as additive potassium hexafluorophosphate and is doped with iron (III) sulphate.

16. Detector of claim 2, suitable for detecting hydrogen sulfide, wherein the said one electrode comprises silver, said polymer is polymethyl methacrylate, and said solvent is propylene carbonate and the electrolyte contains as additive triethanolamine and acetic acid, and is doped with iron (III) sulphate.

17. Detector of claim 2 suitable for measuring sulfide dioxide, wherein the said one electrode comprises silver, said polymer is polyacrylonitrile, and said solvent is propylene carbonate and the electrolyte contains as additive triethanolamine and acetic acid, and is doped with silver sulphate.

18. Detector of claim 2, suitable for measuring sulfur dioxide, wherein the said one electrode comprises silver, said polymer is polyacrylonitrile, and said solvent is γ-butyrolactone, and the electrolyte contains as additives triethanolamine and acetic acid, and is doped with silver sulphate and iron (III) sulphate.

19. Detector of claim 2, suitable for measuring nitrogen dioxide, wherein one electrode comprises carbon and the other electrode comprises gold or carbon, and said polymer is polymethyl methacrylate, and said solvent is phosphoric acid-tris-dimethyl amine, and the electrolyte contains as additive potassium hexafluorophosphate, and is doped with iron (III) sulphate.

20. Detector of claim 2, suitable for measuring oxygen, wherein one electrode comprises silver and the other electrode comprises lead, said polymer is polyacrylonitrile, and said solvent is propylene carbonate, and the electrolyte contains as additive triethanolamine and acetic acid.

21. Detector of claim 2, suitable for measuring hydrogen fluorine, wherein one electrode comprises zirconium and the other electrode comprises zirconium or platinum, said polymer is polymethyl methacrylate, and said solvent is propylene carbonate, and the electrolyte contains as additive acetic acid.

22. Detector of claim 2, suitable for measuring chlorine wherein said one electrode comprises platinum, said polymer is polyacrylinitrile, and said solvent is propylene carbonate, and the electrolyte contains as additives tolylic acid and sodium benzoate, and is doped with iron (III) sulphate, and means for polarizing the electrodes during measurement by the application of a voltage in such a way that only a very weak current flows, so that the flow of depolarization current triggered off by the chlorine is a measure of the concentration of chlorine.

23. Detector of claim 1, wherein the gel has an electrical conductivity of at least $10^{-5}$ ohn$^{-1}$cm$^{-}$, a dielectric constant of at least 20 and a dipole moment of at least 2.0 Debye.

24. Detector of claim 1, comprising a cylinder having a hollow space therein in which there is a ring surrounding the gel electrolyte which is closed off by a measuring electrode on one side which is exposed to the gas to be measured, and by a counter electrode on the other side.

25. Detector of claim 24, wherein the detector is in the form of a throughflow measuring cell having a throughflow element mounted on said cylinder, said throughflow element having an inlet bore for conveying gas to the measuring electrode for passage of gas passed the measuring electrode, and an outlet bore for receiving gas passed by the measuring electrode and discharging the gas from the detector.

26. Detector of claim 1, comprising a member having an opening therein, the gel electrolyte being mounted in said opening, the get electrolyte being provided with a measuring electrode so that a triple phase interface of the gas, measuring electrode and electrolyte is formed on one side of the electrolyte and the other side of the gel electrolyte being provided with a counterelectrode.

27. Detector of claim 26, wherein said opening is cylindrical.

28. Process of measuring the concentration of a reactable component in a gas which comprises contacting the gas with the electrolyte of a detector cell according to claim 1 for reaction of said component to an extent proportional to the concentration of said component in the gas for generation of electric current in said closing circuit to an extend proportional to the concentration of said component in the gas, and measuring an effect on said current as a measure of the concentration of said component in the gas.

29. Process of claim 28, wherein said anhydrous organic gel is based on an anhydrous organic solvent and a synthetic polymer.

30. Process of claim 29, wherein the polymer is a linear-macromolecular substance whose chain length corresponds to a molecular weight of at least 50,000.

31. Process of claim 29, wherein the polymer and solvent are homopolar molecules.

32. Process of claim 29, wherein the gel is doped with a salt which dissociates in the organic solvent for the polymer.

33. Process of claim 32, wherein the salt is $KPF_6$.

34. Process of claim 29, wherein the organic solvent contains a carbonyl, alkoxyl, hydroxyl or phosphoric acid ester group.

35. Process of claim 29, wherein the polymer is a homopolymer of an olefinically unsaturated compound, or a copolymer of olefinically unsaturated compounds.

36. Process of claim 35, wherein the polymer is of at least one monomer of the group monovinyl monomers and monovinylidene monomers.

37. Process of claim 29, wherein the polymer is polyvinyl chloride and the solvent is of the group acetoxy cyclohexane, ethylene glycol diacetate, benzoic acid ethyl ester, γ-butyrolactone, diethylene glycol monobutyl ether, 4,4-dimethyl-1,3-dioxane, methyl cyclohexyl acetate, lactic acid ethyl ester, oxalic acid diethyl ester, propylene carbonate and butylene carbonate.

38. Process of claim 29, wherein the polymer is polyacrylonitrile and the solvent is of the group γ-butyrolactone, caprolactone, 1-methyl-2-pyrrolidone, phosphoric acid-tris-dimethyl amide, propylene carbonate and butylene carbonate.

39. Process of claim 29, wherein the polymer is polymethyl methacrylate and the solvent is of the group acetoxy cyclohexane, benzoid acid ethyl ester, γ-butyrolactone, caprolactone, diethylene glycol monobutyl ether, 2,2-dimethyl-3-butanone, 4,4-dimethyl-1,3-dioxane, 2,2-dimethyl-4-hydroxy methyl-1,3,-dioxolane, 1-methyl-4-cyclohexanol, methyl cyclohexanone, methyl cyclohexyl acetate, 1-methyl-2-pyrrolidone, lactic acid ethyl ester, phosphoric acid-tris-dimethyl amide, propylene carbonate and butylene carbonate.

40. Process of claim 29, suitable for detecting hydrogen sulfide, wherein said one electrode comprises silver, and said polymer is polymethyl methacrylate or polyacrylonitrile, and said solvent is propylene carbonate, and the electrolyte contains as additive sodium benzoate and benzoid acid, and is doped with iron (III) sulphate.

41. Process of claim 29, suitable for detecting hydrogen sulfide, wherein said one electrode comprises silver, and said polymer is polyacrylonitrile, and said solvent is γ-butyrolactone, and the electrolyte contains as additives sodium benzoate and benzoic acid and is doped with iron (III) sulphate.

42. Process of claim 29, suitable for detecting hydrogen sulfide, wherein said one electrode comprises silver, said polymer is polymethyl metharcylate, and said solvent is propylene carbonate or phosphoric acid-tris-dimethyl amine, and the electrolyte contains as additive potassium hexaflurorphosphate and is doped with iron (III) sulphate.

43. Process of claim 29, suitable for detecting hydrogen sulfide, wherein the said one electrode comprises silver, said polymer is polymethyl methacrylate, and said solvent is propylene carbonate and the electrolyte contains as additive triethanolamine and acetic acid, and is doped with iron (III) sulphate.

44. Process of claim 29, suitable for measuring sulfur dioxide, wherein the said one electrode comprises silver, said polymer is polyacrylonitrile, and said solvent is propylene carbonate and the electrolyte contains as additive triethanolamine and acetic acid, and is doped with silver sulphate.

45. Process of claim 29, suitable for measuring sulfur dioxide, wherein the said one electrode comprises silver, said polyer is polyacrylonitrile, and said solvent is γ-butyrolactone, and the electrolyte contains as additives tirethanolamine and acetic acid, and is doped with silver sulphate and iron (III) sulphate.

46. Process of claim 29, suitable for measuring nitrogen dioxide, wherein one electrode comprises carbon and the other electrode comprises gold or carbon, and said polymer is polymethyl methacrylate, and said solvent is phosphoric acid-tris-dimethyl amine, and the electrolyte contains as additive potassium hexafluro-phosphate, and is doped with iron (III) sulphate.

47. Process of claim 29, suitable for measuring oxygen, wherein one electrode comprises silver and the other electrode comprises lead, said polymer is poolyacrylonitrile, and said solvent is propylene carbonate, and the electrolyte contains as additive triethanolamine and acetic acid.

48. Process of claim 29, suitable for measuring hydrogen fluoride, wherein one electrode comprises zirconium and the other electrode comprises zirconium or platinum, said polymer is polymethyl methacrylate, and said solvent is propylene carbonate, and the electrolyte contains as additive acetic acid.

49. Process of claim 29, suitable for measuring chloride wherein said one electrode comprises platinum, said polymer is polyacrylonitrile, and said solvent is propylene carbonate, and the electrolyte contains as additives tolylic acid and sodium benzoate, and is doped with iron (III) sulphate, and means for polarizing the electrodes during measurement by the application of a voltage in such a way that only a very weak current flows, so that the flow of depolarization current triggered off by the chlorine is a measure of the concentration of chlorine.

50. Process of claim 28, wherein the gel has an electrical conductivity of at least $10^{-5}$ ohm$^{-1}$cm$^{-1}$, a dielectric constant of at least 20 and a dipole moment of at least 2.0 Debye.

51. Process of claim 28, the detector cell comprising a cylinder having a hallow space therein in which there is a ring surrounding the gel electrolyte which is closed off by a measuring electrode on one side which is exposed to the gas to be measured, and by a counter electrode on the other side.

52. Process of claim 51, wherein the detector is in the form of a throughflow measuring cell having a throughflow element mounted on said cylinder, said throughflow element having an inlet bore for conveying gas to the measuring electrode for passage of gas passed the measuring electrode, and an outlet bore for receiving gas passed by the measuring electrode and discharging the gas from the detector.

53. Process of claim 28, the detector cell comprising a member having an opening therein, the gel electrolyte being mounted in said opening, the gel electrolyte being provided with a measuring electrode so that a triple phase interface of the gas, measuring electrolde and electrolyte is formed on one side of the electrolyte and the other side of the gel electrolyte being provided with a counter-electrode.

54. Process of claim 53, wherein said opening is cylindrical.

* * * * *

UNITED STATES PATENT AND TRADEMARK OFFICE
CERTIFICATE OF CORRECTION

PATENT NO. : 4,049,503

DATED : September 20, 1977

INVENTOR(S) : Wolf-Jürgen Becker et al

It is certified that error appears in the above-identified patent and that said Letters Patent are hereby corrected as shown below:

Column 1, line 23, "compound" should read -- component --.

Column 2, line 39, "particle" should read -- particles --.

Column 2, line 46, "Stauffs" should read -- Stauff --.

Column 3, line 15, "dissoved" should read -- dissolved --.

Column 3, line 22, insert -- freely -- after "oscillate".

Column 4, line 27, "exits" should read -- exists --.

Column 5, line 36, "plasticityand" should read -- plasticity and --.

Column 8, line 10, "Examle" should read -- Example --.

Column 8, line 14, "resitance" should read -- resistance --.

Column 8, line 65, "Remark" should read -- Remarks --.

Column 9, line 4, "Remark" should read -- Remarks --.

Column 9, line 8, move "$5 \times 10^6$" to next column.

Column 9, line 8, move "$1 \times 10^6$" to next column.

Column 10, line 13, "butyrolwactone" should read -- butyrolactone --.

Column 10, line 43, "ester" should read -- ether --.

Column 10, line 43, "butanione" should read -- butanone --.

Column 10, line 48, "adide" should read -- amide --.

UNITED STATES PATENT AND TRADEMARK OFFICE
CERTIFICATE OF CORRECTION

PATENT NO. : 4,049,503

DATED : September 20, 1977

INVENTOR(S) : Wolf-Jürgen Becker et al

It is certified that error appears in the above-identified patent and that said Letters Patent are hereby corrected as shown below:

Column 10, line 54, "benzoid" should read -- benzoic --.

Column 10, line 67, "potasium" should read -- potassium --.

Column 11, line 7, "sulfide" should read -- sulfur --.

Column 11, line 33, "fluorine" should read -- fluoride --.

Column 11, line 40, "polyacrylinitrile" should read -- polyacrylonitrile --.

Column 11, line 50, "ohn" should read -- ohm --.

Column 12, line 14, "extend" should read -- extent --.

Column 12, line 48, "solventis" should read -- solvent is --.

Column 12, line 54, "benzoid" should read -- benzoic --.

Column 12, line 67, "benzoid" should read -- benzoic --.

Column 13, line 29, "polyer" should read -- polymer --.

Column 13, line 31, "tirethanolamine" should read -- triethanolamine --.

Column 13, lines 42-43, "poolacrylonitrile" should read -- polyacrylonitrile --.

UNITED STATES PATENT AND TRADEMARK OFFICE
CERTIFICATE OF CORRECTION

PATENT NO. : 4,049,503  Page 3 of 3
DATED : September 20, 1977
INVENTOR(S) : Wolf-Jürgen Becker et al It is certified that error appears in the above—identified patent and that said Letters Patent are hereby corrected as shown below:

Column 14, lines 7-8, "chloride" should read -- chlorine --.

Column 14, line 39, "electrolde" should read -- electrode --.

Signed and Sealed this

Sixteenth Day of May 1978

[SEAL]

Attest:

RUTH C. MASON
Attesting Officer

LUTRELLE F. PARKER
Acting Commissioner of Patents and Trademarks